United States Patent
Chen et al.

(10) Patent No.: US 9,669,242 B2
(45) Date of Patent: Jun. 6, 2017

(54) COMPOSITIONS CONTAINING AT LEAST TWO PHENOLIC COMPOUNDS, A LIPID-SOLUBLE ANTIOXIDANT AND AT LEAST ONE HYDROTROPE FOR COSMETIC USE

(71) Applicant: L'OREAL, Paris (FR)

(72) Inventors: Nannan Chen, Princeton, NJ (US); Patricia Brieva, Manalapan, NJ (US); Donna McCann, Oxford, NJ (US); Anthony Potin, Hoboken, NJ (US)

(73) Assignee: L'OREAL, Paris (FR)

( * ) Notice: Subject to any disclaimer, the term of this patent is extended or adjusted under 35 U.S.C. 154(b) by 320 days.

(21) Appl. No.: 13/932,272

(22) Filed: Jul. 1, 2013

(65) Prior Publication Data

US 2015/0005247 A1    Jan. 1, 2015

(51) Int. Cl.

| | |
|---|---|
| A61K 31/7028 | (2006.01) |
| A61K 31/70 | (2006.01) |
| A61K 31/7042 | (2006.01) |
| A61K 8/60 | (2006.01) |
| A61K 8/34 | (2006.01) |
| A61K 8/49 | (2006.01) |
| A61Q 19/08 | (2006.01) |
| A61K 8/67 | (2006.01) |
| A61K 8/891 | (2006.01) |

(52) U.S. Cl.
CPC .............. *A61Q 19/08* (2013.01); *A61K 8/347* (2013.01); *A61K 8/498* (2013.01); *A61K 8/4953* (2013.01); *A61K 8/675* (2013.01); *A61K 8/678* (2013.01); *A61K 8/891* (2013.01)

(58) Field of Classification Search
CPC ...... A61K 8/347; A61K 8/4953; A61K 8/498; A61K 8/602; A61Q 19/08
USPC ...................................... 514/27, 25; 536/4.1
See application file for complete search history.

(56) References Cited

U.S. PATENT DOCUMENTS

| | | | |
|---|---|---|---|
| 3,501,409 A | | 3/1970 | Matson |
| 3,839,210 A | | 10/1974 | Beiswanger et al. |
| 4,680,143 A | | 7/1987 | Edge et al. |
| 5,532,012 A | | 7/1996 | Balentine et al. |
| 5,686,082 A | | 11/1997 | N'Guyen |
| 5,773,014 A | * | 6/1998 | Perrier et al. ............... 424/401 |
| 6,121,209 A | | 9/2000 | Watts et al. |
| 6,331,520 B1 | | 12/2001 | Richardson |
| 6,355,657 B1 | | 3/2002 | Osborne |
| 6,423,327 B1 | | 7/2002 | Dobson, Jr. et al. |
| 6,479,442 B1 | | 11/2002 | Berube et al. |
| 6,624,342 B1 | * | 9/2003 | Grimm ................... C12N 9/00 435/419 |
| 6,645,513 B2 | | 11/2003 | Dobson, Jr. et al. |
| 6,646,035 B2 | | 11/2003 | Koch et al. |
| 6,733,797 B1 | | 5/2004 | Summers |
| 6,949,496 B1 | | 9/2005 | Boutique et al. |
| 7,452,549 B2 | | 11/2008 | Hasler-Nguyen et al. |
| 2002/0086042 A1 | | 7/2002 | Delrieu et al. |
| 2002/0110604 A1 | | 8/2002 | Babish et al. |
| 2003/0031715 A1 | | 2/2003 | Park et al. |
| 2003/0206972 A1 | | 11/2003 | Babish et al. |
| 2004/0146474 A1 | | 7/2004 | Galey |
| 2005/0158271 A1 | | 7/2005 | Lee et al. |
| 2005/0266121 A1 | | 12/2005 | Lines et al. |
| 2006/0110439 A1 | | 5/2006 | Tobia et al. |
| 2007/0208088 A1 | | 9/2007 | Lipshutz |
| 2007/0232561 A1 | | 10/2007 | Leung et al. |
| 2008/0095866 A1 | | 4/2008 | Declercq et al. |
| 2008/0176956 A1 | | 7/2008 | Hsu |
| 2008/0219927 A1 | | 9/2008 | Thakur et al. |
| 2009/0110674 A1 | | 4/2009 | Loizou |
| 2009/0233876 A1 | | 9/2009 | Auriol et al. |
| 2010/0047297 A1 | | 2/2010 | Petersen |
| 2011/0033525 A1 | | 2/2011 | Liu |
| 2011/0067294 A1 | | 3/2011 | Ng et al. |
| 2011/0136245 A1 | | 6/2011 | Parker |
| 2011/0152214 A1 | | 6/2011 | Boison et al. |
| 2012/0071550 A1 | | 3/2012 | Zelkha et al. |
| 2012/0283226 A1 | * | 11/2012 | Buckley et al. .............. 514/161 |

FOREIGN PATENT DOCUMENTS

| | | | |
|---|---|---|---|
| CN | 102210632 A | * | 10/2011 |
| WO | WO-2013016257 A1 | | 1/2013 |

OTHER PUBLICATIONS

Shi et al; CN 102210632 A; Oct. 12, 2011; (Machine English Translation).*
Suzuki, H. et al., "Mechanistic Studies on Hydrotropic Solubilization of Nifedipine in Nicotinamide Solution," *Chem. Pharm. Bull.* 46(1), 125-130 (1998).
Evstigneev, M.P. et al., "Effect of a mixture of caffeine and nicotinamide on the solubility of vitamin (B2) in aqueous solution," *European Journal of Pharmaceutical Sciences* 28, 59-66 (2006).
Da Silva, R.C. et al., "Investigations on the mechanism of aqueous solubility increase caused by some hydrotropes." *Thermochimica Acta* 328. 161-167 (1999).

(Continued)

*Primary Examiner* — Shaojia Anna Jiang
*Assistant Examiner* — Michael C Henry
(74) *Attorney, Agent, or Firm* — Polsinelli PC

(57) ABSTRACT

The present invention relates to compositions comprising: (a) at least two phenolic compounds (one flavoid and one non-flavoid); (b) at least one hydrotrope; (c) at least one emulsifier; (d) a lipid-soluble antioxidant; and (e) water. The at least one hydrotrope should be present in an amount that is effective to solubilize said at least two phenolic compounds in the water phase of the composition. The at least one emulsifier should be present in an amount sufficient to create a water-in-oil or oil-in-water emulsion that is effective to solubilize the lipid-soluble antioxidant. The compositions are useful for cosmetic purposes and other uses.

17 Claims, 1 Drawing Sheet

(56) References Cited

OTHER PUBLICATIONS

Huh, K.M. et al., "A new hydrotropic block copolymer micelle system for aqueous solubilization of paclitaxel," *Journal of Controlled Release* 126, 122-129 (2008).
Takahashi, K. et al., "Application of hydrotropy to transdermal formulations: hydrotropic solubilization of polyol fatty acid monoesters in water and enchantment effect on skin permeation of 5-FU," *Journal of Pharmacy and Pharmacology* 63, 1008-1014 (2011).
Nicoli, S. et al., "Association of nicotinamide with parabens: Effect of solubility, partition and transdermal permeation," *European Journal of Pharmaceutics and Biopharmaceutics* 69, 613-621 (2008).
Nidhi, K. et al., "Hydrotropy: A Promising Tool for Solubility Enhancement: A Review," *International Journal of Drug Development & Research* 3(2), 26-33 (2011).

\* cited by examiner

COMPOSITIONS CONTAINING AT LEAST TWO PHENOLIC COMPOUNDS, A LIPID-SOLUBLE ANTIOXIDANT AND AT LEAST ONE HYDROTROPE FOR COSMETIC USE

BACKGROUND OF THE INVENTION

The present invention relates to compositions comprising: (a) at least two phenolic compounds (one flavoid and one non-flavoid); (b) at least one hydrotrope; (c) at least one emulsifier; (d) a lipid-soluble antioxidant; and (e) water. The at least one hydrotrope should be present in an amount that is effective to solubilize said at least two phenolic compounds in the water phase of the composition. The at least one emulsifier should be present in an amount sufficient to create a water-in-oil or oil-in-water emulsion that is effective to solubilize the lipid-soluble antioxidant. The compositions are useful for cosmetic purposes.

The formation of free radicals is a widely accepted pivotal mechanism leading to skin aging. Free radicals are highly reactive molecules with unpaired electrons that can directly damage various cellular membranes, lipids, proteins, RNA and DNA. The damaging effects of these reactive oxygen species are induced internally during normal metabolism and externally through various oxidative stresses. UV exposure and environmental pollution can accelerate skin aging by producing free radicals in skin. Antioxidants protect cells from the damage of oxidative stress by scavenging free radicals and inhibiting following oxidation reactions. As skin ages, the endogenous ability to protect against oxidative stress declines, and makes it necessary to provide extra help to counteract oxidative stress produced both internally and externally. The topical application of antioxidants is broadly used in skin care products to prevent skin aging.

Phenolic compounds (i.e., phenols and polyphenols), the most abundant antioxidants in diet, are well known as very effective antioxidants. They have been widely studied in the prevention of degenerative diseases, particularly cardiovascular diseases and cancers. Many phenolic compounds have been formulated in nutrition supplements and consumer products. However, the solubility of most phenolic compounds is very limited, especially in water, which diminishes their applications and biological potential in cosmetics. Thus, there is a need for methods of increasing the water solubility of phenolic compounds.

Applications and biological potential of many phenolic compounds in cosmetics are limited due to their poor solubility. Various delivery systems, such as gel carriers (US application publication 20020086042), or nano crystals (US application publication 2010/0047297), or chemical modification of the polyphenols (US application publications 20090233876, 20080095866, and 20080176956) have been used to obtain better solubility of phenolic compounds. However, these approaches have drawbacks. Some are tied to specific delivery systems. Modification of phenolic compounds increases costs, the improvement of solubility is still limited, and modifications can reduce the activity of the phenolic compounds.

Other solutions to the problem of poor solubility include the use of solubilizers such as strong organic solvents (U.S. Pat. No. 5,532,012) and diterpene glycosides (US application publication 2011/0033525). Nevertheless, these solutions do not have good safety, and are not necessarily compatible with cosmetic formulations. Moreover, most of the time, when water is added to such compositions, the solubility of the phenolic compounds decreases dramatically.

Thus, there remains a need for methods for improving the water solubility of phenolic compounds, including polyphenols, for cosmetic and other uses. Further, in order to provide a more complete protection against oxidative stress to the skin, a lipid-soluble antioxidant is desirable to protect against lipid peroxidation, which helps to maintain the integrity of cell membranes. Vitamin E (sometimes referred to commercially as "tocopherol") is an essential fat-soluble vitamin that includes eight naturally occurring compounds in two classes designated as tocopherols and tocotrienols. It is a powerful antioxidant. α-tocopherol is the most abundant biologically active form of Vitamin E. The antioxidant properties of Vitamin E mainly function at the cellular membrane level because its lipid solubility enables it to be incorporated into the lipid layer of the cell membrane. However, to incorporate a lipid or fat-soluble antioxidant like Vitamin E into a stable aqueous or water-based composition or formulation, it is necessary to create an emulsion. The emulsions described hereinafter are suitable to create stable compositions or formulations that incorporate both the water-soluble phenolic compounds, the at least one hydrotrope and the lipid or fat-soluble antioxidant (e.g., Vitamin E) for cosmetic use.

The terms "fat-soluble", "lipid-soluble" and "oil-soluble" are used synonymously throughout this application, as are the terms "fat", "lipid" and "oil".

BRIEF SUMMARY OF THE INVENTION

The present invention relates to compositions comprising: (a) at least two phenolic compounds (one flavoid and one non-flavoid); (b) at least one hydrotrope; (c) at least one emulsifier; (d) a lipid-soluble antioxidant; and (e) water. The at least one hydrotrope should be present in an amount that is effective to solubilize said at least two phenolic compounds in the water phase of the composition. The at least one emulsifier should be present in an amount sufficient to create a water-in-oil or oil-in-water emulsion that is effective to solubilize the lipid-soluble antioxidant. The compositions are useful for cosmetic purposes. The at least one hydrotrope can be a cosmetically acceptable hydrotrope, such as nicotinamide (niacinamide), caffeine, sodium PCA, sodium salicylate, urea, or hydroxyethyl urea. In one aspect of the present invention, the at least one hydrotrope is at least one substance selected from nicotinamide (niacinamide), caffeine, sodium PCA, and sodium salicylate. The at least two phenolic compounds include at least baicalin and resveratrol but can also include any other type of phenol or polyphenol as long as that further phenol or polyphenol does not have a detrimental effect on the composition.

Another aspect of the invention provides a method for preparing a composition comprising including in said composition: (i) water; (ii) at least two phenolic compounds (one flavoid and one non-flavoid); (iii) a lipid-soluble antioxidant; (iv) at least one hydrotrope in an amount that is effective to solubilize said at least two phenolic compounds in the water phase of the composition; and (v) at least one emulsifier in an amount sufficient to create a water-in-oil or oil-in-water emulsion that is effective to solubilize the lipid-soluble antioxidant.

A further aspect of the invention provides a method comprising applying a composition to skin (e.g., human skin), the composition comprising: (i) water; (ii) at least two phenolic compounds (one flavoid and one non-flavoid); (iii)

a lipid-soluble antioxidant; (iv) at least one hydrotrope in an amount that is effective to solubilize said at least two phenolic compounds in the water phase of the composition; and (v) at least one emulsifier in an amount sufficient to create a water-in-oil or oil-in-water emulsion that is effective to solubilize the lipid-soluble antioxidant.

These and other aspects of the invention are set out in the appended claims, and described in greater detail in the detailed description of the invention.

DETAILED DESCRIPTION OF THE INVENTION

Figure 1:
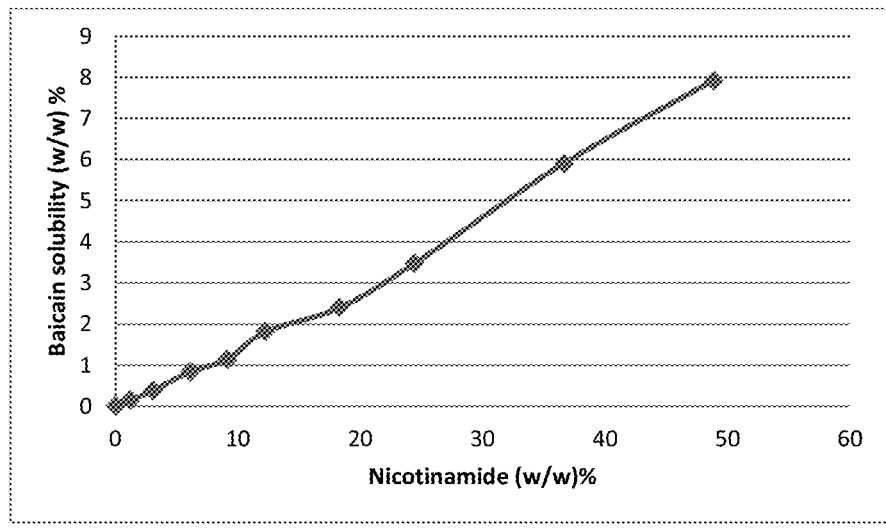
FIG. 1 shows a graph of baicalin solubility as a function of nicotinamide concentration.

The present invention relates to compositions comprising: (a) at least two phenolic compounds (one flavoid and one non-flavoid); (b) at least one hydrotrope; (c) at least one emulsifier; (d) a lipid-soluble antioxidant; and (e) water. The at least one hydrotrope should be present in an amount that is effective to solubilize said at least two phenolic compounds in the water phase of the composition. The at least one emulsifier should be present in an amount sufficient to create a water-in-oil or oil-in-water emulsion that is effective to solubilize the lipid-soluble antioxidant (i.e., in the oil or lipid phase of the emulsion). The compositions are useful for cosmetic purposes and other purposes. The hydrotrope, such as a cosmetically acceptable hydrotrope, improves the water solubility of the phenolic compounds. The hydrotropes can be used to formulate phenolic compounds, especially polyphenols, in all cosmetic formulations that contain water, for topical application or injection, and food applications, such as beverages.

Most phenolic compounds, including polyphenols, have very limited solubility (<0.1%) in water depending on their various structures. Applicants have discovered that hydrotropes can dramatically increase the solubility of these poorly water-soluble phenolic compounds in water by orders of magnitude. Thus, water-containing compositions containing effective amounts of a hydrotrope can contain phenolic compounds in greater percentage amounts than water-containing compositions in which a hydrotrope is not present. Applicants have also found that combinations of hydrotropes, such as the combination of caffeine and nicotinamide (niacinamide), are more efficient than either hydrotrope alone for increasing the water solubility of phenolic compounds.

Hydrotropes (or hydrotropic agents) are a diverse class of water-soluble compounds that are characterized by an amphiphilic molecular structure and the ability to dramatically increase the solubility of poorly soluble organic molecules in water.

Most hydrotropes have aromatic structure with an ionic moiety, while some of them are linear alkyl chains, as listed in the table below. Although hydrotropes noticeably resemble surfactants and have the ability to reduce surface tension, their small hydrophobic units and relatively shorter alkyl chain distinguish them as a separate class of amphiphiles. Consequently their hydrophobicity is not sufficient enough to create well organized self-associated structures, such as micelles, even with a high concentration.

Common hydrotropic molecules include: sodium PCA (sodium DL-2-pyrrolidone-5-carboxylate), sodium 1,3-benzenedisulfonate, sodium benzoate, sodium 4-pyridinecarboxylate, sodium salicylate, sodium benzene sulfonate, caffeine, sodium p-toluene sulfonate, sodium butyl monoglycolsulfate, 4-aminobenzoic acid HCl, sodium cumene sulfonate, N,N-diethylnicotinamide, N-picolylnicotinamide, N-allylnicotinamide, 2-methacryloyloxyethyl phosphorylcholine, resorcinol, butylurea, pyrogallol, N-picolylacetamide 3.5, procaine HCl, proline HCl, nicotinamide (niacinamide), pyridine, 3-picolylamine, sodium ibuprofen, sodium xylenesulfonate, ethyl carbamate, pyridoxal hydrochloride, sodium benzoate, 2-pyrrolidone, ethylurea, N,N-dimethylacetamide, N-methylacetamide, and isoniazid. Hydrotropes can be found in Lee J. et al., "Hydrotropic Solubilization of Paclitaxel: Analysis of Chemical Structures for Hydrotropic Property", Pharmaceutical Research, Vol. 20, No. 7, 2003; and Lee S. et al., "Hydrotropic Polymers: Synthesis and Characterization of Polymers Containing Picolylnicotinamide Moieties", Macromolecules, 36, 2248-2255, 2003.

Cosmetically acceptable hydrotropes refers to hydrotropes that can be used in cosmetic compositions. While hydrotropes represent a broad class of molecules used in various fields, cosmetic applications will be limited due to safety and tolerance restrictions. Suitable hydrotropes for use in cosmetics include, but are not limited to, the hydrotropes listed below:

| Name of hydrotropes | Structure |
| --- | --- |
| Nicotinamide (Vit. B3) | 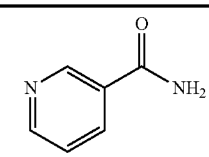 |
| Caffeine | 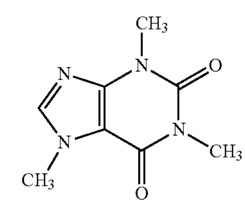 |
| Sodium PCA | 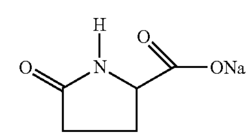 |
| Sodium Salicylate | 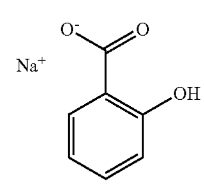 |
| Urea | 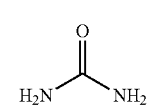 |
| Hydroxyethyl urea | 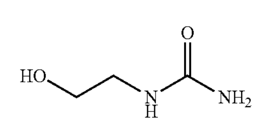 |

The suitability of a hydrotrope for use in cosmetic compositions can be determined using tests known in the art for determining effects on skin, and toxicity to humans.

At least one hydrotrope refers to one or a combination of two or more hydrotropes. One or combination of two or more hydrotropes can be used to improve the solubility of phenolic compounds in water.

The at least one hydrotrope is present in the composition in amounts effective to increase the solubility of the phenolic compound in water. The amount of hydrotrope(s) will vary depending on the hydrotrope(s) and the type and amount of phenolic compound. The amount of hydrotrope(s) present in the compositions can range from about 0.1% to about 15%; about 0.1% to about 10%; or about 1% to about 5%, based on the total weight of the composition. In one aspect of the invention, the at least one hydrotrope is a combination of niacinamide and caffeine, wherein the combination is present in an amount of about 0.2-15%; about 1-10%; about 3-9% or about 4-8% by weight, based on the total weight of the composition. Niacinamide can be present in the combination in amounts of from about 1-10%; about 3-8% or 5-7% by weight, based on the total weight of the composition. Caffeine can be present in the combination in amounts of from about 0.5-7%; about 1-5% or 2-4% by weight, based on the total weight of the composition.

Increasing the water solubility of the phenolic compounds refers to increasing the solubility of the phenolic compounds in water in comparison with solubility of the phenolic compounds in water in the absence of the hydrotrope or hydrotropes.

An advantage of using hydrotropes is that once a stable solution is obtained, further dilution doesn't influence the stability of the solution. This is very different from organic solvents that are commonly used to increase the water solubility of phenolic compounds, such as polyphenols. Typically, an aqueous dilution of organic solvents with pre-dissolved phenolic compound(s), such as a polyphenol, results in crystallization or precipitation.

Phenolic compounds are a structural class of natural, synthetic, and semisynthetic organic compounds that have one or more phenolic constituents. Phenolic compounds containing multiple phenol groups are known as polyphenols. Polyphenols are normally available in plants and are very helpful to protect plants and also animals from usual health disorders and also the impacts of aging. Polyphenols function as potent free radical scavengers by donating their alcoholic hydrogen or one of their delocalized electrons. The two classes of polyphenols are flavonoids and non-flavonoids.

Flavonoids are a specific group of polyphenols, and are the most plentiful group of polyphenol compounds, making up about two-thirds of the total phenols in consumed feed. Flavonoids are further categorized, according to chemical structure, into chalcones, flavones (e.g., baicalin), flavanones, flavanols, flavonols, dihydroflavonols, isoflavonoids, neoflavonoids, catechins, anthocyanidins, and tannins. Over 4,000 flavonoids have been identified, many of which occur in fruits, vegetables and beverages (tea, coffee, beer, wine and fruit drinks). The flavonoids have been reported to have antiviral, anti-allergic, antiplatelet, anti-inflammatory, anti-tumor and antioxidant activities. Flavonoids protect lipids and vital cell components from damaging oxidative stress by efficiently scavenging free radicals.

Non-flavonoid polyphenols include lignans, aurones, stilbenoids, curcuminoids and other phenylpropanoids. Many of them are also well-known antioxidants like resveratrol, curcumin, and pinoresinol.

Other phenolic compounds, in addition to polyphenols, include alkylphenols, betacyanins, capsacinoids, hydroxybenzoketones, methoxyphenols, naphthoquinones, and phenolic terpenes. Some popular examples are ferulic acid, hydroxytyrosol, cinnamic acid, caffeic acid, and p-coumaric acid.

The at least two phenolic compounds are solubilized in the water phase of the compositions, and the amount of phenolic compounds that are solubilized will depend on the specific phenolic compounds and the type and amount of hydrotrope(s) present in the compositions. The amount of phenolic compounds present in the compositions can range from about 0.01% to about 10%; about 0.1% to about 10%; or about 0.1% to about 5%, based on the total weight of the composition.

The lipid-soluble antioxidant present in the composition can be any lipid-soluble antioxidant that helps to protect the skin, especially against lipid peroxidation. The lipid-soluble antioxidant can be present in the composition in amounts of from 0.0001% to 6 by weight. When the lipid-soluble antioxidant is Vitamin E (or tocopherol), it is solubilized in the lipid (i.e., oil) phase of the emulsion, usually in amounts of from 0.0001% to 3% by weight or 0.01% to 2% by weight of the composition.

In general, useful emulsifiers for the composition of the present invention are those with an HLB (hydrophilic-lipophilic balance) no greater than 7. Although any cosmetically acceptable emulsifier with an HLB no greater than 7 can be used in the compositions, excellent results can be obtained using silicone based emulsifiers (sometimes referred to herein as "silicone emulsifier"). Examples of some useful silicone emulsifiers are: (1) dimethicone and PEG/PPG-18/18 dimethicone (e.g., X-22-6711D from Shin-Etsu); (2) dimethicone and dimethicone crosspolymer (e.g., Dow Corning 9041 Silicone Elastomer Blend); (3) dimethicone and dimethicone/PEG-10/15 crosspolymer (KSG-210 from Shin-Etsu); and (4) dimethicone and dimethicone/polyglycerin-3 crosspolymer (KSG 710 from Shin-Etsu).

The compositions can also comprise at least one additive conventionally used in the cosmetics field which does not affect the properties of the compositions according to the invention, such as thickeners, fragrances, pearlescent agents, preservatives, sunscreens, anionic or nonionic or cationic or amphoteric polymers, proteins, protein hydrolysates, fatty acids, such as 18-methyleicosanoic acid, vitamins, panthenol, silicones, vegetable, animal, mineral or synthetic oils, gelling agents, antioxidants, solvents, fragrances, fillers, screening agents, odor absorbers and coloring materials. These additives can be present in the composition according to the invention in proportions which are not limited, but which advantageously fall in the range from 0 to 50% by weight, with respect to the total weight of the composition.

When additional solvents are used, the additional solvents can be mixtures of solvents, such as alcohols, glycols or mixtures thereof. Mixtures of one or more alcohols and one or more glycols can be useful, as are mixtures of one or more glycols or one or more alcohols. Such mixtures can contain virtually any combination of relative amounts of each individual alcohol or glycol. For example, when a mixture of two glycols are used, the relative amounts of each glycol in the mixture can be from 30-70%, 40-60%, 45-55% or even approximately equal amounts (i.e., a 50/50 mixture) of each glycol.

The composition comprises from about 20 to 80% by weight of water, with respect to the total weight of the composition. The amount of water in the composition can also range from about 20 to 60%; or about 30 to 50%, based on the total weight of the composition.

The pH of the water phase of the compositions is not limited but is generally between 2 and 8, or between 3 and 6. The pH can be adjusted to the desired value by addition of a base (organic or inorganic) to the composition, for example ammonia or a primary, secondary or tertiary (poly) amine, such as monoethanolamine, diethanolamine, triethanolamine, isopropanolamine or 1,3-propanediamine, or alternatively by addition of an inorganic or organic acid, advantageously a carboxylic acid, such as, for example, citric acid.

Generally, any composition of the invention can be topically applied to the skin (over any cutaneous region of the body).

For topical application to the skin (e.g., human skin), the composition can have the form in particular of aqueous or oily solutions or of dispersions of the lotion or serum type, of emulsions with a liquid or semi-liquid consistency of the milk type, obtained by dispersion of a fatty phase in an aqueous phase (O/W) or vice versa (W/O), or of suspensions or emulsions with a soft consistency of the aqueous or anhydrous gel or cream type. These compositions are prepared according to the usual methods.

The amounts of the various constituents of the compositions according to the invention are those conventionally used in the fields under consideration.

In the cosmetics field, these compositions constitute in particular creams for cleaning, protecting, treating or caring for the face, for the hands, for the feet, for the major anatomical folds or for the body (for example, day creams, night creams, make-up-removing creams, foundation creams or sun creams), liquid foundations, make-up-removing milks, protective or care body milks, sun milks, lotions, gels or foams for caring for the skin, such as cleansing lotions, sun lotions, artificial tanning lotions, bath compositions, deodorizing compositions comprising a bactericidal agent, aftershave gels or lotions, depilatory creams, compositions for countering insect stings or bites, pain-relieving compositions or compositions for treating certain skin diseases, such as eczema, rosacea, psoriasis, lichen and severe pruritus.

Another aspect of the invention provides a method for preparing the compositions comprising including in said composition: (i) at least two phenolic compounds (one flavoid and one non-flavoid); (ii) a lipid-soluble antioxidant; (iii) at least one hydrotrope in an amount that is effective to solubilize said at least two phenolic compounds in the water phase of the composition; and (iv) at least one emulsifier in an amount sufficient to create a water-in-oil or oil-in-water emulsion that is effective to solubilize the lipid-soluble antioxidant. The general method for preparing the compositions of the present invention involves preparing separately a water-based solution and an oil or lipid-based solution and then bringing the two solutions together under mixing to form an emulsion (water-in-oil or oil-in-water). Other ingredients, especially those ingredients that may be sensitive to certain process conditions used to form the emulsion or those ingredients for which it is beneficial to solubilize the ingredient in another medium before adding to water or oil, can be added to the emulsion with mixing after the emulsion is formed. For example, in one aspect of the present invention, an aqueous hydrotrope solution is prepared by completely dissolving one or more hydrotropic agents into water. In a separate oil or lipid-based solution, one or more of the phenolic compounds are dissolved in an emulsifier (e.g., a silicone emulsifier), along with any other oil or lipid-soluble substances that are appropriate. The aqueous hydrotrope solution and the oil or lipid-based solution are then added together and mixed to form an emulsion. Once the emulsion is prepared, other substances or solutions of substances in other solvents (e.g., alcohols and/or glycols) can be added to the emulsion and mixed to form a final emulsion. In each stage of the process, mixing can be carried out by any appropriate method known in the art (e.g., using a stiffing bar or any other mixing device).

In one aspect of the present invention, the solubilization of at least one of the phenolic compounds in water occurs within minutes and mixing is continued until the maximum concentration of the phenolic compound(s) in the water is achieved, which is defined as the solubility of the phenolic compound(s) under the conditions present. A clear stable solution with a concentration that does not exceed the solubility is usually achieved after more than one hour of mixing. No heat is necessary by following this procedure to dissolve the phenolic compound(s) in the water. Everything is prepared at room temperature to maintain the stability of the phenolic compound(s). This is extremely useful to protect the activity of certain phenolic compounds and also makes the process much easier. Once the phenolic compound(s) are fully solubilized in the water, the aqueous solution can be mixed with the oil or lipid-based solution to form the emulsion. In the aspect of the present invention where the at least two phenolic compounds in the composition are baicalin (e.g., scutellaria baicalensis extract/scutellaria baicalensis root extract; Baicalin 95MM) and resveratrol, hydrotropes that may be used include caffeine, nicotinamide (niacinamide), sodium PCA and sodium salicylate. However, in this aspect of the invention it may be helpful to first dissolve the resveratrol in a solvent (e.g., one or more glycols or a mixture of one or more glycols and denatured alcohol) before contacting the resveratrol with water. For example, the resveratrol can be first dissolved in a solvent system such as a mixture of two or more glycols (e.g., propylene glycol and dipropylene glycol) and denatured alcohol and then that solution can be added to the emulsion, thus allowing the dissolved resveratrol to become associated with the water phase of the emulsion.

In general, useful emulsifiers for the composition of the present invention are cosmetically acceptable emulsifiers with an HLB (hydrophilic-lipophilic balance) no greater than 7. In the aspect of the present invention where the lipid-soluble antioxidant is Vitamin E (or tocopherol), a useful silicone emulsifier is PEG/PPG-18/18 dimethicone (e.g., X-22-6711D from Shin-Etsu) in combination with dimethicone. Other useful silicone emulsifiers are: dimethicone and dimethicone crosspolymer (e.g., Dow Corning 9041 Silicone Elastomer Blend); dimethicone and dimethicone/PEG-10/15 crosspolymer (KSG-210 from Shin-Etsu); and dimethicone and dimethicone/polyglycerin-3 crosspolymer (KSG 710 from Shin-Etsu).

In one aspect of the present invention, the composition comprises: (a) baicilin and resveratrol as phenolic compounds; (b) niacinamide and caffeine as hydrotropes; (c) dimethicone and PEG/PPG-18/18 dimethicone as the silicone emulsifier; (d) Vitamin E (or tocopherol) as lipid-soluble antioxidant; and (e) water. In another aspect of the present invention, the composition comprises: (a) 0.001-10% by weight of baicalin and 0.0001-2% by weight of resveratrol; (b) 1-5% by weight niacinamide and 0.5-5% by weight caffeine; (c) 0.1-30% by weight of dimethicone (0.65 to 1000 cst) and 0.1-30% by weight of dimethicone crosspolymer as the silicone emulsifier; (d) 0.0001-3% by weight of Vitamin E (or tocopherol) as lipid-soluble antioxidant; and (e) 30 to 60% by weight water.

In other aspects of the present invention, the composition comprises: (a) 0.01-5% by weight or 0.1-1% by weight or 0.1-0.8% by weight of baicalin and 0.01-2% by weight or 0.1-2% by weight or 0.1-1.5% by weight of resveratrol; (b) 1-5% by weight niacinamide and 0.5-5% by weight caffeine; (c) 1-30% by weight or 1-18% by weight or 14-17% by weight of dimethicone (0.65 to 1000 cst) and 3-20% by weight or 3-10% by weight or 6-8% by weight of dimethicone crosspolymer as the silicone emulsifier; (d) 0.01-3% by weight or 0.1-3% by weight or 0.1-2% by weight of Vitamin E (or tocopherol) as lipid-soluble antioxidant; and (e) 30 to 60% by weight or 40-60% by weight water.

In one aspect of the present invention, when the composition contains a silicone emulsifier which is a combination of dimethicone (0.65 to 1000 cst) and dimethicone crosspolymer, the combination is usually used in an amount of from about 4 to about 50% by weight of the composition or from about 4 to about 30% by weight of the composition.

EXAMPLES

Example 1

Solubility Increase of Baicilin in Water Using Hydrotrope

Baicalin, a component of Chinese medicinal herb Huang-chin, is a flavone, a type of flavonoid. It is a potent antioxidant that demonstrates potent effects against oxidative stress diseases, inflammation, allergy, cancer, bacterial infections, etc. However, its solubility in water is extremely low (<0.01% at its natural pH ~4.5), especially at low pH, as shown below, and degradation happens at pH>5.

| | PH | | | | |
|---|---|---|---|---|---|
| | 3 | 3.5 | 4 | 4.5 | 5 |
| solubility | 0.0016% | 0.0021% | 0.0040% | 0.0084% | 0.035% |

Although certain organic solvents can increase the solubility of baicalin, such as PEG-4 which can dissolve 3% baicalin, a dilution of these solutions in water is not stable any more. Crystallization or precipitation occurs after mixing the glycol phase and water phase.

The solubility of baicalin in water can be increased by raising the concentration of hydrotropes. In contrast to what happens in organic solvents, such aqueous solutions are still stable if diluted in water.

Water solubility of baicalin was increased as a function of nicotinamide concentration as shown in FIG. 1.

Figure 2:
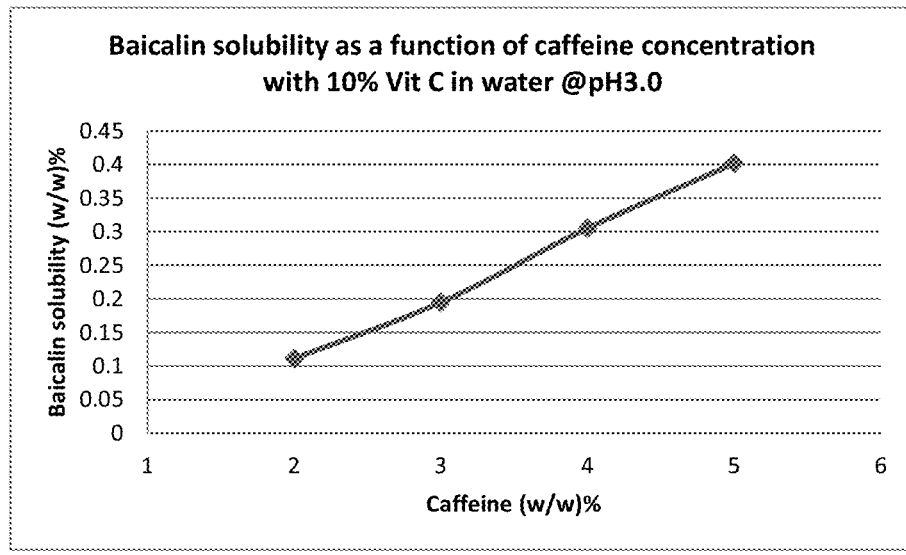
FIG. 2 shows a graph of baicalin solubility as a function of caffeine concentration.

2% (w/w) caffeine in water improved the water solubility of baicalin from <0.01% to 0.11%; and further improvement was observed as more caffeine was dissolved in water with 10% Vit. C, shown in FIG. 2.

Example 2

Increase in Caffeine Solubility in Water Using Nicotinamide (Niacinamide)

The water solubility of caffeine is approximately 2%, which limited its function as a hydrotropic agent. By mixing with nicotinamide (niacinamide), the solubility of caffeine can be increased to 5% or higher. And the combination of caffeine and nicotinamide is more efficient than either hydrotrope alone for increasing the water solubility of phenolic compounds. The combination of 5% nicotinamide and 5% caffeine in water solubilized approximately 1% baicalin in water, which dramatically increased the water solubility of baicalin by more than 100 times.

The combination of hydrotropes, 5% nicotinamide and 5% caffeine, has been found to be very efficient to increase the water solubility of numerous polyphenols, including flavonoid and non-flavonoid polyphenols, and other phenolic compounds.

The water-solubility results for several phenolic compounds with this combination of hydrotropes are listed in the table below.

| Phenolic Compound | Type | Solubility in water without hydrotropes % (w/w) | Solubility in water with hydrotropes % (w/w) |
|---|---|---|---|
| Baicalin | flavones | <0.01 | >1 |
| Taxifolin | dihydroflavonols | <0.1 | >1 |
| Neohesperidin | dihydrochalcone | <0.05 | >1 |
| Resveratrol | stilbenoids | <0.005 | >0.75 |
| Ellagic acid | tannins | <0.001 | >0.01 |
| Ferulic acid | Phenolic acid | <0.1 | >2 |

Example 3

Compatibility of the Polyphenol/Hydrotrope Complex in Different Systems

Preparation A: Serum

| Phase | Component | Weight % of total |
|---|---|---|
| A | Propylene glycol | 10 |
| A | Dipropylene glycol | 10 |
| A | Ethanol | 10 |
| B | Water | 59.5 |
| B | Nicotinamide | 5 |
| B | Caffeine | 5 |
| B | Baicalin | 0.5 |

Preparation A was prepared as follows. The glycol phase (Phase A) components were mixed together at room temperature. At the same time, the aqueous phase (Phase B) components were mixed at room temperature until a clear solution was obtained. The glycol phase was then added into the aqueous phase with constant stirring for another one hour, and the desired serum was obtained.

Preparation B: O/W Emulsion (Cream)

| Phase | Component | Weight % of total |
|---|---|---|
| A1 | Water | 58.5 |
| A1 | Nicotinamide | 5 |
| A1 | Caffeine | 5 |
| A1 | Baicalin | 0.5 |
| A2 | Glycerin | 10 |
| A2 | Xanthan gum | 0.2 |
| A2 | Preservatives | 1 |
| B | Dicaprylyl carbonate | 3 |
| B | Dimethicone | 3 |
| B | Dicapryl alcohol and ceteareth-20 | 4 |
| B | Glyceryl stearate and PEG-100 stearate | 4.5 |
| C | Dimethicone ammonium | 4 |
| C | Polyacryloyldimethyl taurate | 0.3 |
| D | Nylon-12 | 1 |

Preparation B was prepared as follows. Phase A1 components were mixed at room temperature until a clear solution was obtained. In separate containers, Phase A2 was pre-suspended and then added into Phase A1 with constant stirring and heated to 65° C. At the same time, Phase B components were mixed and completely dissolved at 65° C. Then Phase B was added into Phase A and emulsified for 10-15 minutes. Heating was stopped, and mixing was continued when Phase C was added and mixed for another 10 minutes. Phase D was added after the temperature was below 40° C., and mixed for 10-15 minutes (side sweep) or until powders were fully dispersed, and the desired emulsion was obtained.

Preparation C: W/Si Emulsion (Gel)

| Phase | Component | Weight % of total |
|---|---|---|
| A | BIS-PEG/PPG-14/14 DIMETHICONE (and) DIMETHICONE | 4 |
| A | Dimethicone (and) dimethiconol | 1 |
| A | Dimethicone | 10 |
| B1 | Water | 43.95 |
| B1 | Nicotinamide | 5 |
| B1 | Caffeine | 5 |
| B1 | Baicalin | 0.5 |
| B2 | Glycerin | 15 |
| B2 | Propylene glycol | 5 |
| B3 | Water | 5 |
| B3 | Preservatives | 0.25 |
| B3 | Sodium citrate | 0.2 |
| B3 | Sodium chloride | 0.8 |
| C | Ethanol | 3 |
| C | Preservatives | 0.6 |
| D | Silica silylate | 0.7 |

Preparation C was prepared as follows. Phase A components were mixed together at room temperature. Phase B1 and Phase B2 were premixed in separate containers at room temperature until clear solutions were obtained. Phase B3 was mixed while heating it to 75-80° C. until it was clear. Phase B2 and Phase B3 were added into Phase B1 while mixing. Then Phase B was slowly added into Phase A while mixing (as viscosity increased, the mixing speed was appropriately increased). When the addition was finished, mixing was continued for an additional 10 minutes before adding pre-mixed Phase C. Phase D was slowly added while mixing until it was thoroughly dispersed, and the desired emulsion was obtained.

Example 4

Composition According to the Present Invention
Preparation D: W/Si Emulsion (Gel)

| Phase | Component | Weight % of Total |
|---|---|---|
| A | DIMETHICONE and PEG/PPG-18/18 DIMETHICONE | 22.5 |
| B | WATER | 41.9 |
| B | DISODIUM EDTA | 0.1 |
| B | SODIUM CHLORIDE | 2 |
| B | NIACINAMIDE AND CAFFEINE | 7 |
| B | *SCUTELLARIA BAICALENSIS* EXTRACT/*SCUTELLARIA BAICALENSIS* ROOT EXTRACT | 0.50 |
| B | GLYCERIN | 3 |
| C | GLYCOLS | 16 |
| C | RESVERATROL | 1 |
| C | ALCOHOL DENAT. | 5 |
| D | TOCOPHEROL | 1 |

Preparation D was prepared as follows. In a main vessel, phase A was mixed with a homogenizer. In a separate vessel, phase B was mixed until all solids were completely dissolved. The pH of phase B was then adjusted to 4.5±0.1 with NaOH. In another side vessel, phase C was mixed until the Resveratrol was completely dissolved. Phase B was then slowly added to phase A to create an emulsion, which was mixed until uniform. Phase C was then gradually added to the main vessel while mixing. Phase D was then gradually added to the main vessel while mixing. The mixing was continued after the addition of phase D until the mixture was uniform and a stable emulsion was present.

The three primary antioxidant ingredients in preparation D (i.e., baicalin, resveratrol and tocopherol) were subjected together as a mixture to in tubo antioxidant testing to determine the antioxidant activity of the mixture. The tests, known as ORAC and HORAC, are described below.

ORAC

The Oxygen Radical Absorbance Capacity (ORAC) assay is one of most commonly used methods to evaluate the capacity of antioxidants against ROS (reactive oxygen species), specific for peroxyl which is one of the most important free radicals present in the human skin environment.

The ORAC assay measures the oxidative degradation of the fluorescent probe (fluorescein) after being mixed with free radical generators such as azo-initiator compounds (2,2'-Azobis(2-amidinopropane)dihydrochloride, AAPH). Azo-initiators are considered to produce the peroxyl radical by heating, which damages the fluorescent molecule, resulting in the loss of fluorescence. Antioxidants are considered to protect the fluorescent molecule from the oxidative degeneration. By quantifying the decay of fluorescence using a fluorometer, the degree of protection is determined comparing with a standard control antioxidant Trolox. The result is expressed in μmol equivalent of Trolox per gram of sample (i.e., μmolTE/g). Equipment that can automatically measure and calculate the capacity is commercially available, such as the VarioSkan flash microplate reader from Thermo Scientific.

To test samples by using ORAC, compounds are dissolved into water-based $NaH_2PO_4$ buffer.

HORAC

The HORAC assay is another common method to examine antioxidant activity. It is specific for hydroxyl radicals.

The Varioskan Flash is employed for the quantification of the capacity of an antioxidant to avert the hydroxyl radical. The hydroxyl radical, generated from hydrogen peroxide and Cobalt (II) fluoride, will quench a fluorescent probe by a hydrogen atom transfer reaction. In the presence of an antioxidant, however, the molecule will chelate the Co(II), preventing the generation of the hydroxyl radical and initially block or prevent the quenching of the probe, causing a delay in the fluorescence decay profile. The area under the fluorescence decay curves for samples with and without the presence of an antioxidant molecule are compared to that of a standard reference material and the hydroxyl radical averting capacity is determined By quantifying the decay of fluorescence using a fluorometer, the degree of protection is determined by comparison with a standard control antioxidant Gallic Acid (standard reference material). The result is expressed in μmol equivalent of Gallic Acid per gram of sample (i.e., μmolGAE/g). Equipment that can automatically measure and calculate the capacity is commercially available, such as the VarioSkan flash microplate reader from Thermo Scientific.

To test samples by using HORAC, compounds are dissolved into water-based $NaH_2PO_4$ buffer.

The results of the tests are shown in the table below.

| Test | Measured Value | Expected Value |
|---|---|---|
| ORAC (μmolTE/g) | 407 | 288 |
| HORAC (μmolGAE/g) | 206 | 155 |

The expected value shown in the above table is the calculated antioxidant activity based on the known activity of each individual antioxidant in the preparation (i.e., the sum of the activities of the 0.5% baicalin; 1% resveratrol and 1% Vitamin E (or tocopherol)). The known activity of each of the antioxidants is shown in the table below. In both the ORAC and HORAC tests, the measured activity was much greater than the expected activity, showing that the combination of these three antioxidants in the preparation provided synergistic antioxidant activity.

Individual Values

| RM Name | ORAC(μmolTE/g) | HORAC (μmolGAE/g) |
|---|---|---|
| VIT. E (tocopherol) | 1000 | N/A |
| Resveratrol | 25462 | 14190 |
| Baicalin | 4759 | 2592 |

The composition of Example 4 (i.e., Preparation D) was subjected to stability tests as described below. The first test was a room temperature stability test. In this test, the samples were held for two months at room temperature in sealed containers (screw top glass vials; 80% full). The second test was an accelerated stability test conducted at 45° C. In the second test, the samples were held at 45° C. for two months in sealed containers (screw top glass vials; 80% full). These conditions are used to simulate holding the samples at room temperature for three years.

The samples from the stability tests were analyzed to determine the levels of the three active ingredients (baicalin, resveratrol and Vitamin E) before and after the tests. The results, which are provided below in the table, showed that the composition of Example 4 was very stable (i.e., there was very little degradation of the active ingredients during the stability tests). A stable composition containing about 1% by weight resveratrol, about 0.5% by weight baicalin and about 1% by weight Vitamin E is very desirable as a cosmetic composition for application to human skin.

| Sample | Test Conditions | Resveratrol Level By Weight of the Composition | Baicalin Level By Weight of the Composition | Vitamin E (or tocopherol) Level By Weight of the Composition |
|---|---|---|---|---|
| Composition of Example 4 | 2 months at room temperature | 0.96% | 0.48% | 1.0% |
| Composition of Example 4 | 2 months at 45° C. | 0.88% | 0.43% | 0.93% |

What is claimed is:

1. A cosmetic composition comprising:
   (a) 0.01 to 5 wt. % baicalin and 0.01 to 2 wt. % resveratrol;
   (b) 0.5 to 5 wt. % caffeine and 1 to 5 wt. % nicotinamide;
   (c) 4 to 50 wt. % of emulsifier;
   (d) 0.01 to 3 wt. % of Vitamin E; and
   (e) 30 to 60 wt. % water,
   wherein the composition is an emulsion.

2. The composition of claim 1, wherein the cosmetic composition is for application to human skin.

3. The composition of claim 1, wherein the emulsifier is a silicone emulsifier.

4. The composition of claim 3, wherein the silicone emulsifier consists essentially of dimethicone and dimethicone crosspolymer.

5. The cosmetic composition of claim 1 comprising:
   (a) 0.1 to 1 wt. % baicalin and 0.1 to 2 wt. % resveratrol;
   (b) 0.5 to 5 wt. % caffeine and 1 to 5 wt. % nicotinamide;
   (c) 4 to 50 wt. % of emulsifier;
   (d) 0.1 to 3 wt. % of Vitamin E; and
   (e) 30 to 60 wt. % water.

6. The composition of claim 5, wherein the cosmetic composition is for application to human skin.

7. The composition of claim 5, wherein the emulsifier is a silicone emulsifier.

8. The composition of claim 5, wherein the silicone emulsifier comprises dimethicone.

9. The composition of claim 5, wherein the silicone emulsifier comprises dimethicone crosspolymer.

10. The cosmetic composition of claim 1 comprising:
    (a) 0.1 to 0.8 wt. % baicalin and 0.1 to 1.5 wt. % resveratrol;
    (b) 0.5 to 5 wt. % caffeine and 1 to 5 wt. % nicotinamide;
    (c) 4 to 50 wt. % of emulsifier;
    (d) 0.1 to 2 wt. % of Vitamin E; and
    (e) 30 to 60 wt. % water.

11. The composition of claim 10, wherein the cosmetic composition is for application to human skin.

12. The composition of claim 10, wherein the emulsifier is a silicone emulsifier.

13. The composition of claim 10, wherein the silicone emulsifier comprises dimethicone.

14. The composition of claim 10, wherein the silicone emulsifier comprises dimethicone crosspolymer.

15. A cosmetic composition comprising:
    (a) 0.01 to 5 wt. % baicalin and 0.01 to 2 wt. % resveratrol;
    (b) 0.5 to 5 wt. % caffeine and 1 to 5 wt. % nicotinamide;
    (c) 1 to 30 wt. % of dimethicone and 3 to 20 wt. % of dimethicone crosspolymer;
    (d) 0.01 to 3 wt. % of Vitamin E; and
    (e) 40 to 60 wt. % water,
    wherein the composition is an emulsion.

16. The cosmetic composition of claim 15, wherein the total amount of the combination of dimethicone and dimethicone crosspolymer is about 4 to about 50 wt. %.

17. The cosmetic composition of claim 15, wherein the total amount of the combination of dimethicone and dimethicone crosspolymer is about 4 to about 30 wt. %.

* * * * *